United States Patent [19]

Ersson

[11] Patent Number: 4,853,137
[45] Date of Patent: Aug. 1, 1989

[54] METHOD AND DEVICE FOR SEPARATING SERUM/PLASMA FROM BLOOD

[76] Inventor: Nils-Olof Ersson, Bokvägen 5, S-961 37 Boden, Sweden

[21] Appl. No.: 50,298
[22] PCT Filed: Aug. 27, 1986
[86] PCT No.: PCT/SE86/00381
§ 371 Date: Apr. 27, 1987
§ 102(e) Date: Apr. 27, 1987
[87] PCT Pub. No.: WO87/01457
PCT Pub. Date: Mar. 12, 1987

[30] Foreign Application Priority Data

Aug. 27, 1986 [SE] Sweden .............................. 8503991

[51] Int. Cl.$^4$ .............................................. B01D 21/26
[52] U.S. Cl. ................................. 210/782; 210/516; 422/101; 422/102; 436/177; 494/16; 494/37; 494/38
[58] Field of Search ............................ 494/16, 37, 38; 422/101, 102; 436/177, 178; 210/782, 789, 516, 787, 518

[56] References Cited

U.S. PATENT DOCUMENTS

| | | | |
|---|---|---|---|
| 3,957,654 | 5/1976 | Ayres | 210/789 X |
| 4,055,501 | 10/1977 | Cornell | 210/516 X |
| 4,088,582 | 5/1978 | Murty et al. | 210/789 |
| 4,190,535 | 2/1980 | Luderer et al. | 210/789 |
| 4,417,981 | 11/1983 | Nugent | 210/516 |

FOREIGN PATENT DOCUMENTS

| | | | |
|---|---|---|---|
| 184274 | 6/1986 | European Pat. Off. | 210/516 |
| 2936107 | 3/1981 | Fed. Rep. of Germany | 210/516 |
| 7900135 | 3/1979 | World Int. Prop. O. | 210/789 |

Primary Examiner—W. Gary Jones
Attorney, Agent, or Firm—Cushman, Darby & Cushman

[57] ABSTRACT

A method and a device for separating the serum included in a certain volume of blood by way of centrifugation. The volume of blood is introduced into a test tube (1) in which a so-called separating body (5; 5') is also present, after which the test tube (1) is centrifugalized. The blood is separated into a heavy phase (11) containing red blood corpuscles and a light phase (12) containing serum or plasma. The separating body (5; 5') is given such a specific gravity that upon centrifugation it enters a position in the boundary layer between the heavy and the light phase (11 and 12, respectively).

A (9; 9') stored in the separating body (5; 5') is moved out of this towards the heavy phase (11) and seals between separating body (5; 5') and test tube (1). When the mass (9; 9') is removed from the separating body (5; 5') a negative pressure will arise therein which is utilized to suck-up accumulated leukocytes and trombocytes into the separating body (5; 5').

2 Claims, 2 Drawing Sheets

METHOD AND DEVICE FOR SEPARATING SERUM/PLASMA FROM BLOOD

BACKGROUND OF THE INVENTION

This invention relates to a method of separating serum/plasma included in a certain volume of blood, said volume of blood being introduced into a test tube, in which a so-called separating body is also present, after which the test tube is centrifugalized, the blood being separated into a heavy phase containing red blood corpuscles and a light phase containing serum or plasma, the separating body being given such a specific gravity that upon centrifugation it enters a position in the boundary layer between the heavy and light phase. The invention also relates to a device for separation according to the above.

A plurality of various technical methods are known to provide separation of a sample of blood enclosed in a test tube to a heavy phase containing red blood corpuscles and a light phase containing serum.

A general method is arranging a silicon compound having a specific gravity between that of the heavy phase and the light phase on the bottom of a test tube. Upon centrifugation of the sample the silicon compound will form a barrier between the heavy phase and the light phase so that the light phase, i.e. the serum/plasma can be removed from the test tube while the heavy phase, i.e. the red blood corpuscles, remains in the test tube. However, this technique does not provide any mechanical barrier between the two phases and, moreover, the accumulation of leukocytes and trombocytes in the boundary layer between the two phases is not taken charge of, meaning that the serum/plasma will be "contaminated" by these leukocytes and trombocytes.

It is also known in separation of the kind described above to use a quite mechanical separating body having such as specific gravity that it will adjust itself upon centrifugation of the test tube in the boundary layer between the heavy and the light phase.

The mechanical separating bodies have different types of seals bearing on the walls of the test tube. However, these seals cannot be made too efficient as the separating body must be able to slide within the test tube. Moreover, the accumulation of leukocytes and trombocytes in the boundary layer between the heavy and the light phase is not taken charge of but will "contaminate" the serum/plasma.

SUMMARY OF THE INVENTION

It is the object of this invention to show a method and a device of the kind mentioned above, where the separation is achieved by means of a separating body providing, on one hand, an adequate mechanical sealing between the two phases and, on the other hand, takes charge of the concentration of leukocytes and trombocytes taking place in a separation through centrifugation.

This object of the invention is realized by a mechod and a device to which have been given the characteristic features defined in the claims.

According to a preferred embodiment of the invention the separating body is arranged in a test tube open at both ends, said ends being sealed by means of elastic members and, as a result of this, vacuum prevailing in the test tube.

BRIEF DESCRIPTION OF THE DRAWING

An illustrative example of the invention will be described below with reference to the enclosed drawings, wherein.

DETAILED DESCRIPTION

Figure 1:
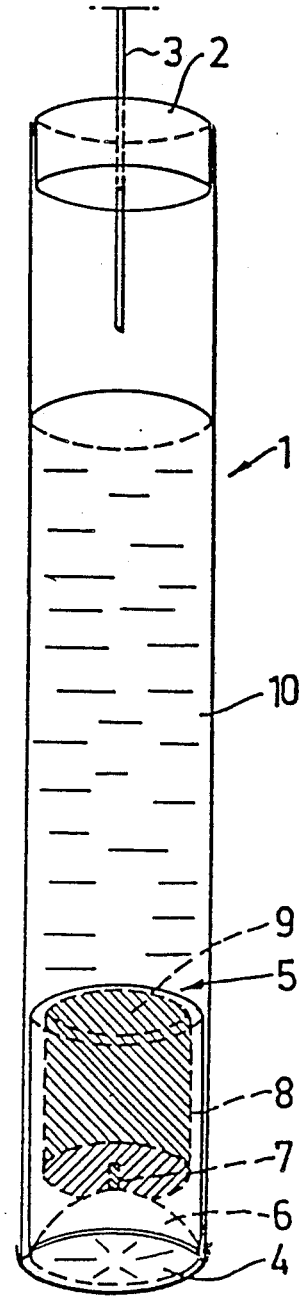
FIG. 1 shows a test tube in which a separating body according to the invention is placed and the test tube is in a position of sampling.
Figure 2:
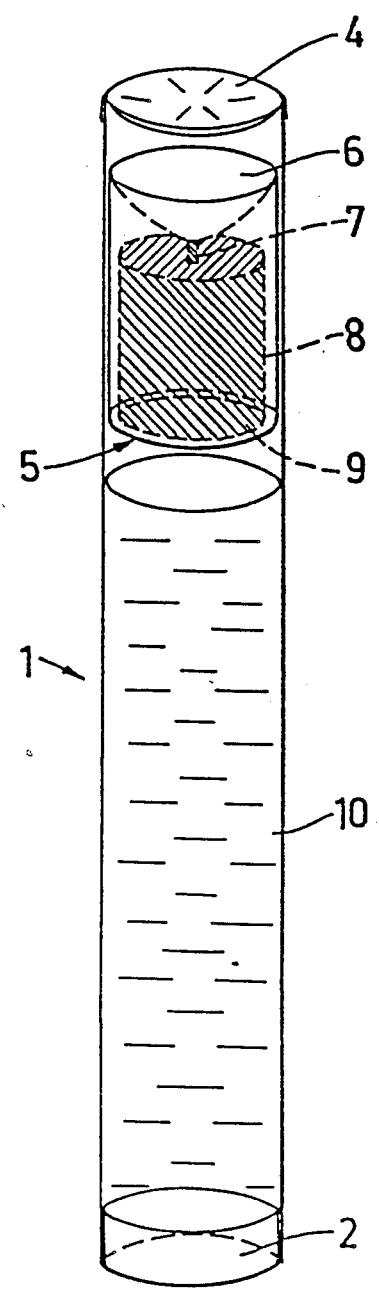
FIG. 2 shows the test tube according to FIG. 1 in a position for separation.
Figure 3:
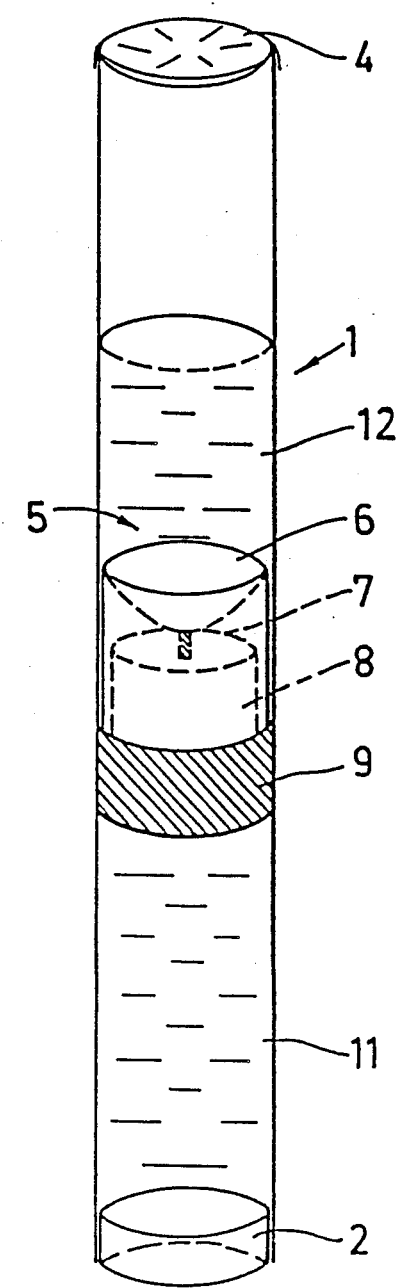
FIG. 3 shows the test tube according to FIG. 1 after separation.

The test tube 1 shown in FIGS. 1–3 is open at its two ends. One end (the upper one in FIG. 1) of the test tube 1 is sealed by means of a plug 2 of an elastic material, said plug 2 being of a type that can be penetrated a plurality of times by a cannula 3 without losing its sealing ability upon removal of the cannula 3.

At the other end of the test tube 1 (the lower one in FIG. 1) a relatively thin membrane 4 of an elastic material is arranged which is threaded onto said end of the test tube 1 to provide a sealing closure.

There is vacuum in the test tube 1 which has the effect that the membrane 4 will bulge inwards towards the tube 1.

A separating body 5 is also placed within the test tube 1. This separating body 5 consists of an outer shell of a shape-permanent material, e.g. rigid plastic, the material of the shell also having the property not to react with blood.

In the illustrative example shown the shell has a cup-shaped recess 6, which is associated with a cylindrical recess 8 by way of a passage 7.

A viscous or, as an alternative, fine granular mass 9 having a specific gravity somewhat higher than the specific gravity of the shell is placed within the cylinder-shaped recess 8.

The test tube 1 with its associated separating body 5 described above is used as follows.

In the starting position shown in FIG. 1 the separating body 5 is located in connection with the membrane 4, i.e. at the lower end of the test tube 1.

A sample of blood 10 is thereafter supplied to the test tube 1 by way of the cannula 3 in FIG. 1, the blood being sucked into the test tube 1 thanks to the vacuum prevailing therein. When a desired quantity of blood has been supplied to the test tube 1 the cannula 3 is removed, and the plug 2 will close the test tube 1 sealingly at its upper end in FIG. 1.

Before separation of the sample of blood through centrifugation of the test tube 1 the test tube is turned upside down so that it enters the position shown in FIG. 2, i.e. the sample 10 is located beneath the separating body 5.

Upon centrifugation the sample of blood will substantially be separated into a heavy phase 11 and a light phase 12, see FIG. 3. The heavy phase consists of red blood corpuscles, erythrocytes, while the light phase consists of serum or plasma.

In the range between the heavy and the light phase a layer of leukocytes and trombocytes is accumulated which, thus, have a specific gravity between that of the red blood corpuscles and that of the serum/plasma.

When the centrifugation is carried out the separating body 5 which, thus, consists of the shell and the viscous or fine granular mass, will also seek out a balance position in the test tube corresponding to its specific gravity which is intermediary in relation to the specific gravity of the red blood corpuscles and that of the serum/plasma.

By giving the separating body 5 a specific gravity substantially coresponding to that of the leukocytes and the trombocytes the separating body 5 will enter a balance position on a level with the layer of leukocytes and trombocytes between the heavy and the light phase.

When the separating body has entered this balance position the mass 9 placed in the recess 8 will move downwards out of the recess 8 during the continued centrifugation. Due to a high viscosity and frictional force this will not take place earlier during the centrifugation.

The mass 9 has a somewhat higher specific gravity than the shell of the separating body 5 but a somewhat lower specific gravity than the heavy phase 11 meaning that the mass 9 will flow at least partly around the lower edge of the shell and seal the space between the separating body 5 and the wall of the test tube.

In this way the red blood corpuscles have been separated efficiently from the rest of the sample of blood in the test tube 1.

When the mass 9 is moved at least partly downwards out of the recess 8 a negative pressure will arise in the part of said recess 8 facing the passage 7. This has the effect that a great portion of the leukocytes and trombocytes accumulated on a level with the separating body 5 will be sucked by way of the cup-shaped recess 6 into the part of the recess 8 where there is negative pressure. This is extremely advantageous as it is desirable that the serum or plasma is freed from leukocytes and trombocytes as much as possible, which are not desired in the analysis which will be made on the serum or plasma.

Thus, when the separation by way of centrifugation is finished substantially only serum/plasma is found above the separating body. This serum/plasma which is thus to be analysed is removed from the test tube preferably by means of a cannula penetrating the membrane 4 and sucking out a desired quantity of serum/plasma. In this way a person handling the test tube 1 need not get in contact with its contents which is a great advantage i.a. in view of the infection risks.

Figure 4:
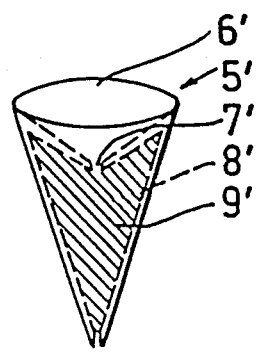
FIG. 4 shows an alternative embodiment of the separating body according to the invention.

In the embodiment of a separating body 5' according to the invention shown in FIG. 4 this has a conical primary form and the recess 8' has also been given such a form. In this illustrative example the cup-shaped recess 6' is directly connected with the recess by way of an aperture 7'.

At its lower end the recess 8' has a relatively small outlet opening for the mass 9' meaning that a mass of a somewhat lower viscosity than in the illustrative example described above can be used in this illustrative example.

To sum up, it can thus be established that the separating body of this invention provides a mechanical barrier between the separated phases through the sealing effect of the mass 9 against the wall of the test tube and that the accumulation of leukocytes and trombocytes is sucked into the recess 8 in the separating body 5 at least partly.

In the illustrative example described the separating body according to the invention is placed in a test tube which is open at both its ends and sealed there by elastic members. Vacuum prevails within the test tube. This arrangement has several advantages as has been stated above. However, it is also possible to use the separating body of the invention at other types of test tubes, but handling thereof will be somewhat more awkward.

Of course the dimensions of the separating body must be adapted to the type of test tube used. As far as the play between the wall of the test tube and the outer periphery of the separating body is concerned a suitable size of this appears to be about 0.5 mm. Of course this is only an indication for the sake of exemplification.

The illustrative examples of separating bodies given above are by no means complete but further embodiments within the scope of the invention are possible, the spherical form being especially worth mentioning.

The invention can also be freely varied in other respects within the scope of the following claims.

What is claimed is:

1. A method for separating serum or plasma from a given volume of blood, comprising:
   providing a test tube having a peripheral sidewall with an inner peripheral surface and two opposite ends;
   disposing in said test tube a separating body including a shell having a first recess which opens axially towards one of said ends, a second recess which opens axially towards the other of said ends, an axially extending internal passage connecting said first and second recesses, and an outer periphery which is spacedly surrounded by said inner peripheral surface of said sidewall, so as to leave an annular gap therebetween; said separating body further including a filling of viscous or fine granular material received in said first recess; said separating body having a specific gravity substantially corresponding to that of leukocytes and thrombocytes contained in the blood that is to be separated; said filling having a higher specific gravity than said shell; said separating body being disposed near said one end of said test tube;
   introducing into said test tube a given volume of blood;
   with said test tube closed, centrifuging the blood-containing test tube in an orientation such as to separate said blood into a heavy phase containing red corpuscles and located between said one end and said separating body and a light phase containing serum or plasma and located between said opposite end and said separating body, plus leukocytes and thrombocytes located in said light phase adjacent said second recess;
   further centrifuging the test tube and its contents, in said orientation, and thereby causing said filling to flow axially out of said first recess and, reversing axial direction, into said annular gap thereby sealing said annular gap, creating a negative pressure in said second recess and causing at least some of said leukocytes and thrombocytes to be sucked into said second recess, whereby light phase relatively free of luekocytes and thrombocytes remains outside said separating body in said test tube, between said separating body and said opposite end.

2. A device for separating serum or plasma from a given volume of blood, comprising:
   a test tube having a peripheral sidewall with an inner peripheral surface and two opposite ends;

a separating body disposed in said test tube, said separating body including a shell having a first recess which opens axially towards one of said ends, a second recess which opens axially towards the other of said ends, an axially extending internal passage connecting said first and second recesses, and an outer periphery which is spacedly surrounded by said inner peripheral surface of said sidewall, so as to leave an annular gap therebetween; said separating body further including a filling of viscous or fine granular material received in said first recess; said separating body having a specific gravity substantially corresponding to that of leukocytes and thrombocytes contained in the blood that is to be separated; said filling having a higher specific gravity than said shell; said separating body being disposed near said one end of said test tube; and means closing both ends of said test tube and being constructed to permit a given volume of blood to be introduced into said test tube, so that, in use, a given volume of blood can be introduced into the test tube and the blood-containing test tube centrifuged in an orientation such as to separate said blood into a heavy phase containing red corpuscles and located between said one end and said separating body and a light phase containing serum or plasma and located between said opposite end and said separating body, plus leukocytes and thrombocytes located in said light phase adjacent said second recess and so that upon further centrifuging in said orientation, said filling flows axially out of said first recess and, reversing axial direction, into said annular gap thereby sealing said annular gap, creating a negative pressure in said second recess and at least some of said leukocytes and thrombocytes are sucked into said second recess, whereby light phase relatively free of leukocytes and thrombocytes remains outside said separating body in said test tube, between said separating body and said opposite end.

* * * * *